United States Patent [19]

Dunsky

[11] 4,293,074
[45] Oct. 6, 1981

[54] ROOT CANAL EQUIPMENT PACKAGING

[76] Inventor: Joel L. Dunsky, 665 Beacon St., Boston, Mass. 02215

[21] Appl. No.: 99,994

[22] Filed: Dec. 4, 1979

[51] Int. Cl.³ .................... B65D 1/34; A45C 11/26
[52] U.S. Cl. ............................... 206/572; 206/369; 206/373; 206/564
[58] Field of Search ............ 206/572, 570, 63.5, 206/564, 565, 804, 499, 223, 369, 373

[56] References Cited

U.S. PATENT DOCUMENTS

| | | | |
|---|---|---|---|
| 3,285,409 | 11/1966 | Loran | 206/63.5 |
| 3,358,826 | 12/1967 | Siegel | 206/570 |
| 3,802,555 | 4/1974 | Grasty et al. | 206/499 |
| 3,982,630 | 9/1976 | Garnier | 206/564 |
| 3,987,895 | 10/1976 | Jamshidi | 206/570 |
| 4,085,845 | 4/1978 | Perfect | 206/804 |
| 4,153,160 | 5/1979 | Leigh | 206/570 |

*Primary Examiner*—William T. Dixson, Jr.
*Attorney, Agent, or Firm*—Charles Hieken

[57] ABSTRACT

A root canal treatment kit includes a lower plastic tray of polystyrene formed with recesses for accommodating root canal treatment apparatus and materials formed with an outermost lip for supporting a transparent cover and an inner lip adjacent the outermost lip upon which legs of an upper plastic tray rest. The upper plastic tray is also formed with recesses for accommodating apparatus and material installing rubber dams in connection with root canal treatment above apparatus on the lower tray. The transparent cover encloses both trays and the root canal treatment apparatus and material stored in the recesses. The rubber dams are installed, then the upper tray is removed, and then the materials and apparatus on the lower tray are used to complete the root canal treatment.

10 Claims, 6 Drawing Figures

ROOT CANAL EQUIPMENT PACKAGING

BACKGROUND OF THE INVENTION

The present invention relates in general to packaging dental equipment and more particularly concerns novel apparatus and techniques for providing a dentist a convenient kit for use in doing root canal work to enable the dentist to have conveniently available in a single package all the instruments and supplies needed for performing root canal work. The invention facilitates safe, sterile, good and economical root canal treatment by a general dental practitioner.

The root canal is a channel in the tooth running from the crown to the root containing the pulp which is composed of connective tissue, nerves and blood vessels. If this pulp tissue is irreversibly damaged by trauma or invasion of decay, root canal treatment is necessary to save the tooth. Treatment typically involves removal of all irritants, necrotic tissue and infected material from the root canal, enlarging and sanitizing the canal, and finally sealing and packing the canal in all dimensions. Root canal treatments are performed by specialists in the field of endodontics. However, a general dentist is capable of administering root canal treatment. Root canal treatment requires a number of specialized instruments, materials and apparatus and maintenance of high standards of sterility to avoid infection. Assembling these materials and equipment to perform a root canal treatment requires considerable time for preparation and assembly of the necessary materials and instruments. Inability to have prompt access to any needed material or instrument delays treatment, extends time needed for treatment and increases cost. Furthermore, this inability in emergency rooms often results in the emergency service offering the patient the alternative of extraction and loss of the tooth or medication to relieve pain until root canal treatment can be obtained.

Accordingly, it is an important object of the invention to provide improved apparatus and techniques that facilitate root canal treatment in a safe and convenient manner.

It is another object of the invention to achieve the preceding object with a convenient kit that contains the materials and apparatus a dentist requires for rendering root canal treatment.

It is still another object of the invention to achieve one or more of the preceding objects with a relatively compact structure that is durable, hygienic, resistant to chemicals used in root canal treatment and relatively lightweight.

It is still a further object of the invention to achieve one or more of the preceding objects with structure that conveniently supports the materials and instruments to provide ready access to them in an organized manner that helps minimize the time required for preparation and administering root canal treatments.

SUMMARY OF THE INVENTION

According to the invention, there is at least first tray means formed with recesses for accommodating the instruments and materials for performing root canal treatment. Another feature of the invention resides in having second tray means overlying the first tray means formed with recesses for accommodating additional instruments and materials above the first tray means, and cover means, preferably transparent, enclosing the first and second tray means and the instruments and materials stored therein.

Numerous other features, objects and advantages of the invention will become apparent from the following specification when read in connection with the accompanying drawing in which:

DETAILED DESCRIPTION OF PREFERRED EMBODIMENTS

Figure 1:
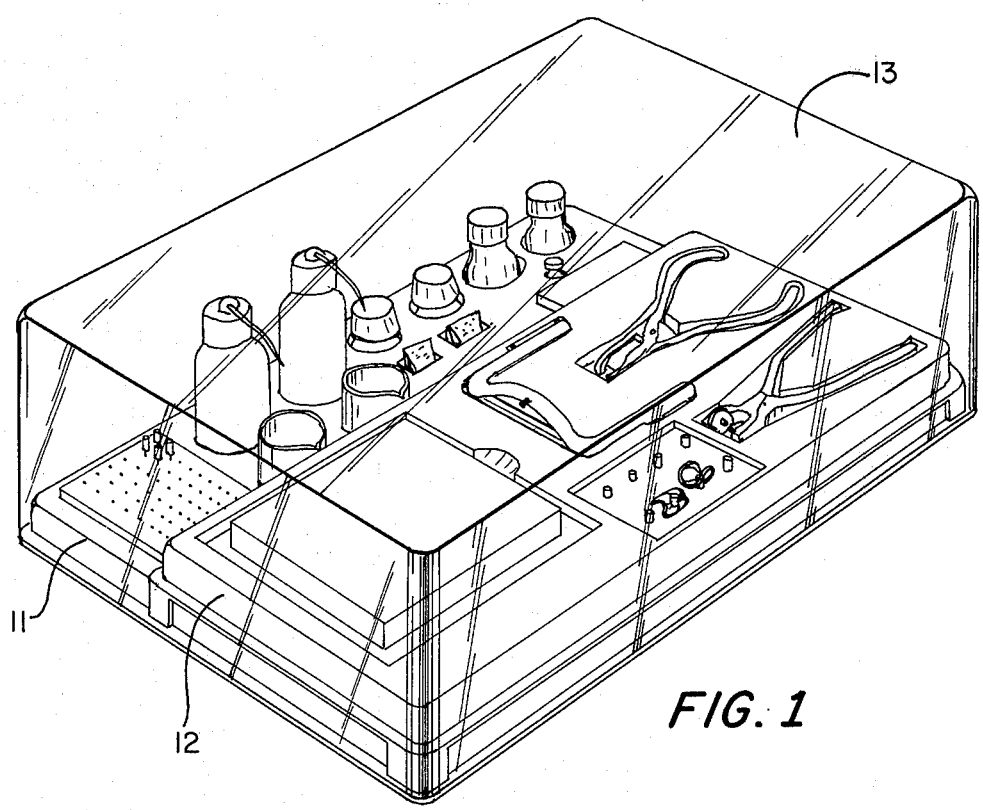
FIG. 1 is a perspective view of a preferred embodiment of the invention.
Figure 2:
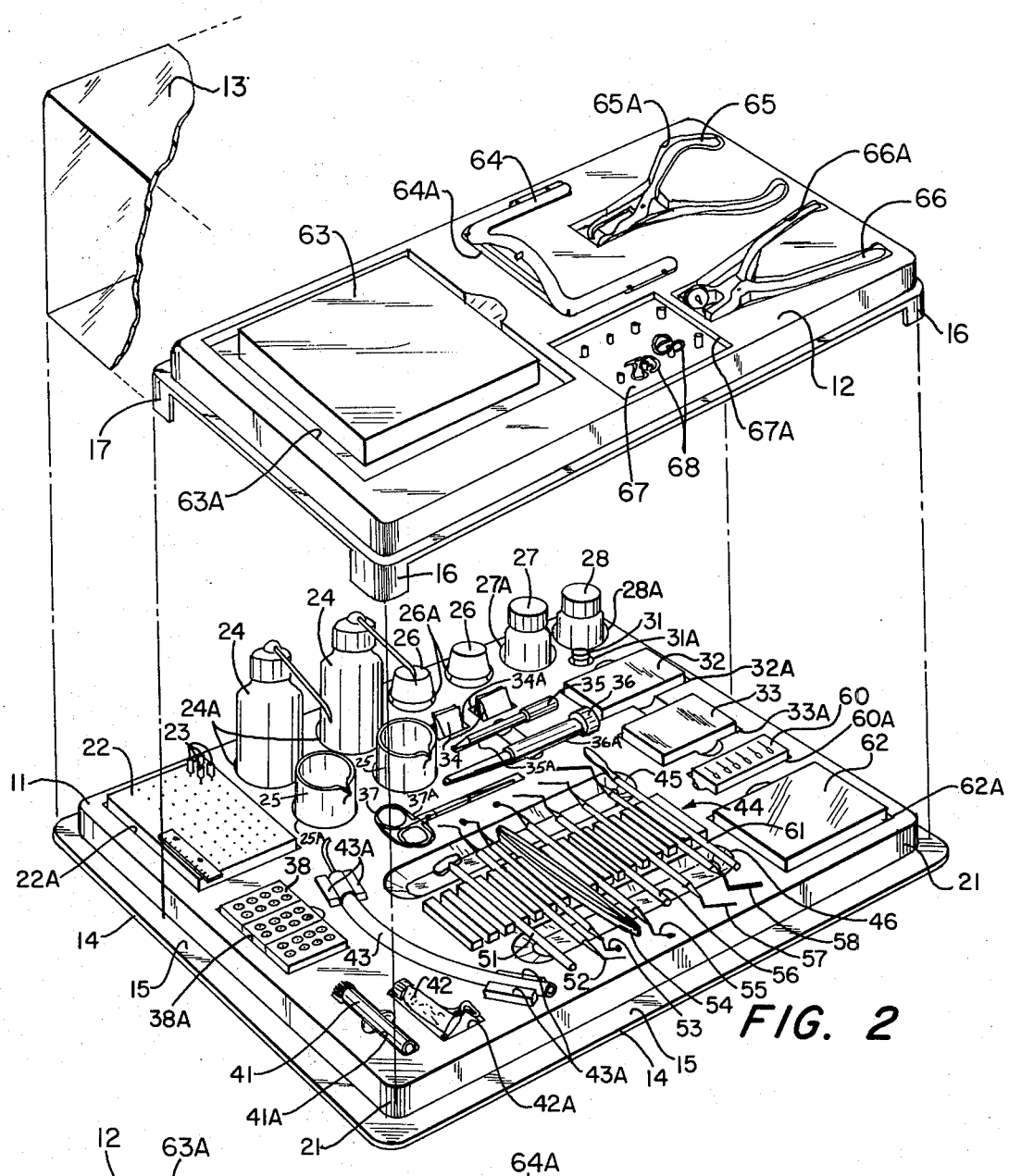
FIG. 2 is an exploded view of the embodiment of FIG. 1 showing the upper tray spaced from the lower tray with the cover fragmentarily illustrated.

With reference now to the drawing and more particularly FIG. 1 thereof, there is shown a perspective view of a preferred embodiment of the invention that is a kit of root canal instruments and materials accommodated in a lower tray 11 and an upper tray 12 covered by a transparent cover 13. The contents of the kit will be better understood from the exploded view of FIG. 2 with cover 13 fragmentarily illustrated to avoid obscuring other structural details. The same reference symbols indentify corresponding elements throughout the drawing. Lower tray 11 is formed with a narrow outside lip or flange 14 for supporting the lower edge of cover 13 and an inner lip or flange 15 for supporting the rounded front corner legs 16 and the rear legs such as 17, corner legs 16 snugly engaging the rounded corners 21 of lower tray 11. Alternatively, the lower tray may be formed with raised projections to prevent horizontal relative movement with the upper tray.

Lower tray 11 includes a number of recesses for accommodating various apparatus and materials. Recess 22A accommodates a file, reamer and broach holder 22 that includes reamers, files and broaches such as 23. Circular recesses 24A accommodate plastic wash bottles 24. Circular recesses 25A accommodate glass stopper medicine bottles 26. Circular recess 27A accommodates a bottle of metacresylacetate 27. Circular recess 28A accommodates a bottle or root canal sealer capsules 28. Circular recess 31A accommodates a vial of sealer liquid such as oil of cloves 31.

Rectangular recess 32A and 33A accommodate a box of absorbent points 32 and a box of gutta percha points 33, respectively. Rectangular recesses 34A accommodate cotton pelletts 35. Recesses 35A and 36A accommodate dropper 35 and irrigating syringe 36, respectively. Recess 37A accommodates scissors 37. Rectangular recess 38A accommodates bur block 38 which carries burs. Recess 41A accommodates wire brush 41. Recess 42A accommodates a tube of temporary filling material 42. The recesses between block pairs 43A accommodate suction 43.

A row of blocks 44 sandwiched by recesses 45 and 46 accommodate a number of instruments, such as mirror 51, DG16 explorer 52, 32L excavator 53, cotton pliers 54, woodson #2 plastic instrument 55, D-11 spreader 56, 5-7 plugger 57, 9-11 plugger 58 and spatula 61. Rectangular recess 60A accommodates finger spreader 60. Rectangular recess 62A accommodates glass slab 62 which may be used for mixing various substances used in the treatment.

In upper tray 12 square recess 63A accommodates two boxes of latex dental dams 63. U-shaped recess 64A accommodates rubber dam frame 64. Y-shaped recess 65A accommodates rubber dam clamp forceps 65. Y-shaped recess 66A accommodates a rubber dam hole puncher 66. Rectangular recess 67A accommodates clamp holder 67 having clamps such as 68.

Figure 3:
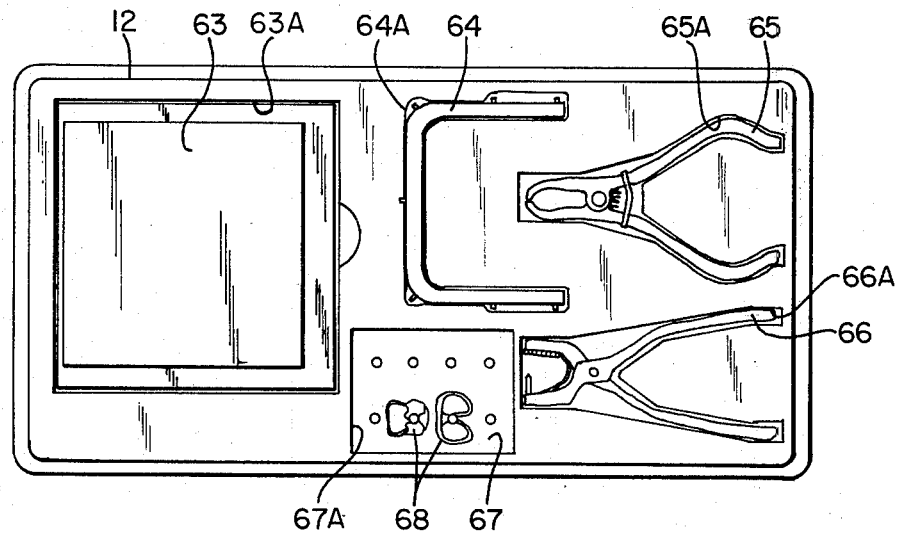
FIG. 3 is a plan view of the upper tray with material and instruments stored therein.
Figure 4:
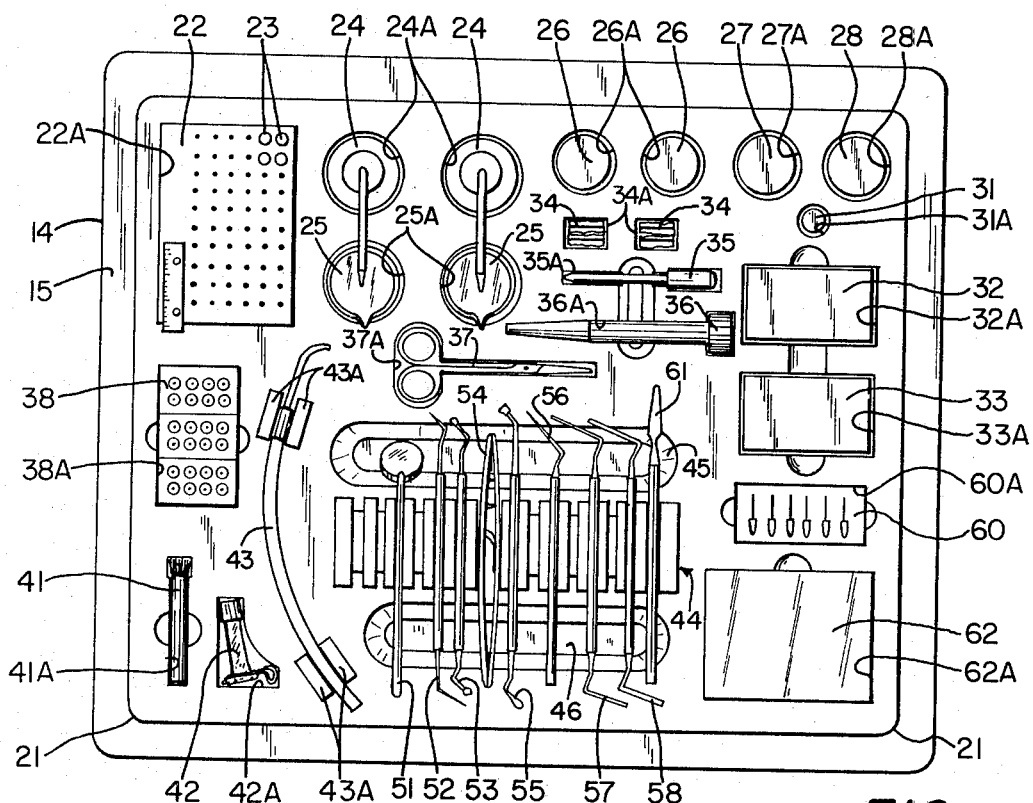
FIG. 4 is a plan view of the lower tray with instruments and materials stored therein.

Referring to FIGS. 3 and 4, there are shown plan views of upper tray 12 and lower tray 11, respectively, and the apparatus and materials therein.

Figure 5:
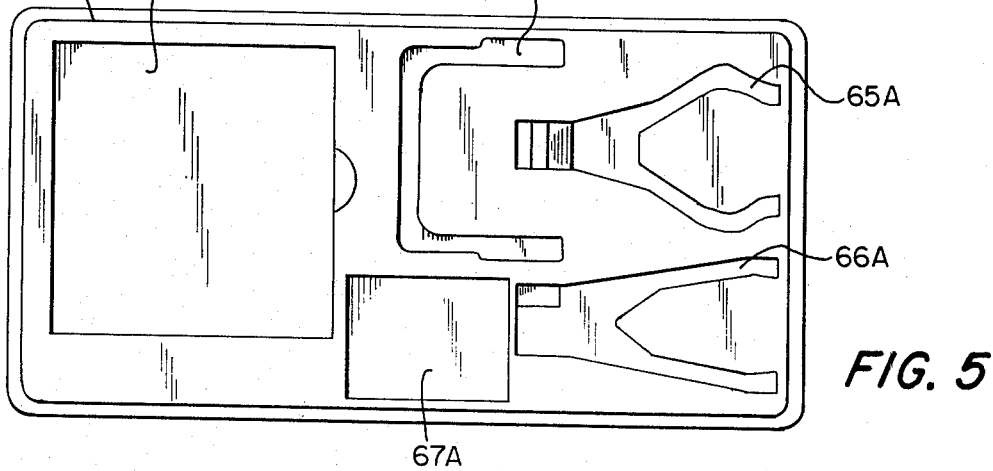
FIGS. 5 and 6 are plan views of the empty top and bottom trays, respectively.
Figure 6:
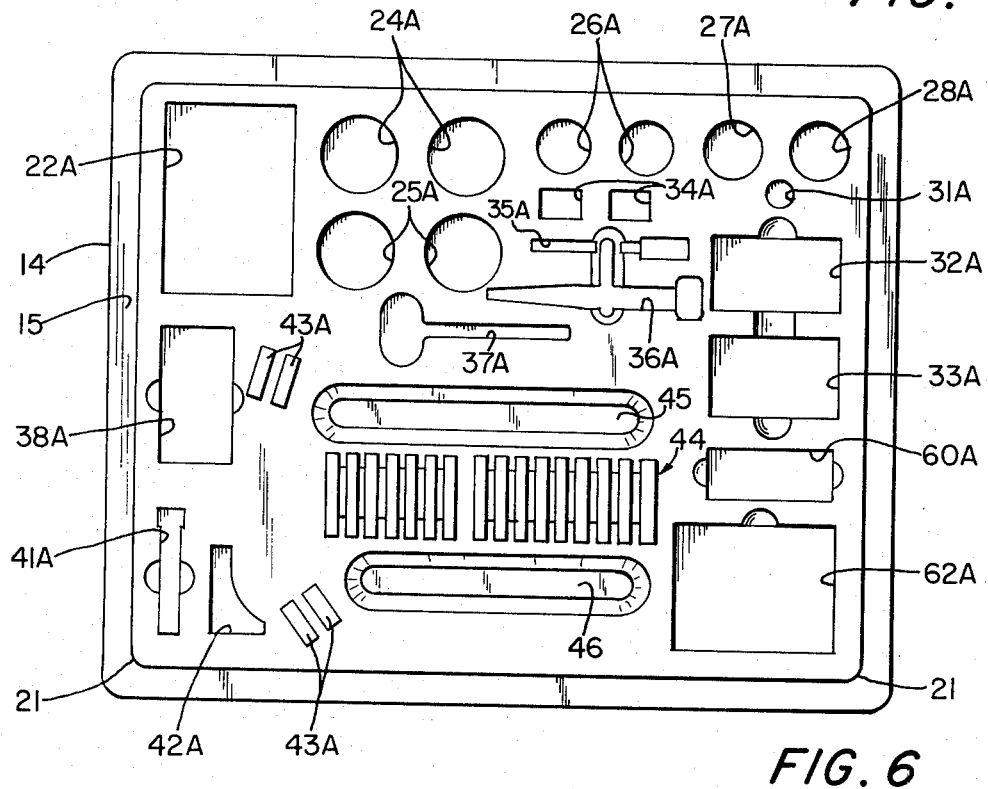

Referring to FIGS. 5 and 6, there are shown plan views of upper tray 12 and lower tray 11, respectively, showing the different recesses.

The kit illustrated and described thus enables a dentist engaged in a general practice trained in root canal treatment to have conveniently available the apparatus and materials for performing root canal treatment in the proper sequence. While the invention is useful for endodontists, it is especially advantageous for a general practitioner who spends most of his working day on other treatments and is thus able to prepare in a short time to administer root canal treatment by moving the kit according to the invention from its usual storage place to a table beside the dental chair, remove protective cover 13, first use the contents of upper tray 12 in installing rubber dams, then lift upper tray 12 from above lower tray 11 and place it beside the latter, thereby readying all the apparatus and materials on lower tray 11 ready for use and conveniently accessible to the dentist for completing the root canal treatment. A suitable material for trays 11 and 12 is coextruded oriented polystyrene laminated to high impact styrene about 0.060 inch thick. The trays may be readily molded, remain sturdy, may be cleansed and are resistant to chemicals used in root canal treatment.

The trays include other features. A number of recesses include adjacent thumb or finger recesses to facilitate removal of items stored there. The structural arrangement of bars 44 and recesses 45 and 46 facilitate removing the different instruments.

It is evident that those skilled in the art may now make numerous modifications of and departures from specific embodiment described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. A root canal treatment kit comprising,
first reusable tray means of plastic material resistant to chemicals used in root canal treatment formed with recesses for accommodating apparatus and materials used in root canal treatment,
second reusable tray means of said plastic material formed with recesses for accommodating said apparatus and materials for root canal treatment formed with means for support by said first tray means spaced above said first tray means by an amount sufficient to allow apparatus and materials for root canal treatment to be accommodated in said recesses in said first tray means when said second tray means is seated thereon,
said second tray means being readily removable from said first tray means,
said recesses accommodating in one package substantially all the instruments and supplies needed by a dentist for performing root canal work.

2. A root canal treatment kit in accordance with claim 1 and further comprising cover means for seating upon said first tray means for coacting with said first tray means to fully enclose the apparatus and material for root canal treatment stored in said recesses.

3. A root canal treatment kit in accordance with claim 1 wherein said first tray means is formed with an outermost lip for accommodating said cover means.

4. A root canal treatment kit in accordance with claim 3 wherein said first tray means is formed with an outermost lip for supporting said cover means and a circumferential inner lip for its perimeter adjacent to said outer lip for supporting depending legs of said second tray means.

5. A root canal treatment kit in accordance with claim 1 and further comprising in respective ones of said recesses a file and reamer block,
a bur block, a wash bottle, a beaker, a dropper, a syringe, explorer, pluggers, spreader, scissors, and a mixing slab.

6. A root canal treatment kit in accordance with claim 5 and further comprising in respective ones of said recesses,
a suction, a wire brush, cotton pliers, a dental mirror and a spatula.

7. A root canal treatment kit in accordance with claim 6 and further comprising,
cotton pellets, absorbent points, gutta percha points and temporary filling material.

8. A root canal treatment kit in accordance with claim 7 and further including said second tray means recesses including a dental dam support,
rubber dam clamp forceps, a rubber dam hole puncher and rubber dam clamps.

9. A root canal treatment kit in accordance with claim 8 wherein said second tray means recesses further include packages of latex dental dam material.

10. A method of using the apparatus of claim 1 which method includes the steps of filling said first tray means with apparatus and materials for use in root canal treatment,
filling said second tray means with apparatus and materials for installing rubber dams in connection with root canal treatment,
placing said second tray means over said first tray means with the latter supporting the former,
positioning the assembly of said first and second tray means beside a patient to be given root canal treatment,
withdrawing the apparatus and materials from said second tray means and using them for installing a rubber dam in the mouth of said patient,
removing said second tray means from said first tray means to expose the apparatus and materials in said first tray means,
withdrawing apparatus and materials from said first tray means and using them for administering root canal treatment to said patient.

* * * * *